United States Patent
Uhde et al.

(10) Patent No.: US 11,202,675 B2
(45) Date of Patent: Dec. 21, 2021

(54) IMPLANT PLACEMENT PLANNING

(71) Applicant: Brainlab AG, Munich (DE)

(72) Inventors: Joerg Uhde, Munich (DE); Thomas Drexl, Poing (DE); Martin Koestler, Munich (DE)

(73) Assignee: BRAINLAB AG, Munich (DE)

( * ) Notice: Subject to any disclaimer, the term of this patent is extended or adjusted under 35 U.S.C. 154(b) by 594 days.

(21) Appl. No.: 16/090,533

(22) PCT Filed: Jun. 14, 2017

(86) PCT No.: PCT/EP2017/064625
§ 371 (c)(1),
(2) Date: Oct. 1, 2018

(87) PCT Pub. No.: WO2018/228689
PCT Pub. Date: Dec. 20, 2018

(65) Prior Publication Data
US 2021/0177517 A1  Jun. 17, 2021

(51) Int. Cl.
*A61B 34/10* (2016.01)
*A61B 34/20* (2016.01)
*A61B 90/00* (2016.01)
*A61B 17/17* (2006.01)

(52) U.S. Cl.
CPC .......... *A61B 34/10* (2016.02); *A61B 17/1757* (2013.01); *A61B 34/20* (2016.02); *A61B 90/36* (2016.02); *A61B 2034/107* (2016.02); *A61B 2034/2068* (2016.02); *A61B 2090/367* (2016.02)

(58) Field of Classification Search
CPC .......... A61B 34/10; A61B 17/17; A61B 34/20; A61B 90/00; G01B 11/24
See application file for complete search history.

(56) References Cited

U.S. PATENT DOCUMENTS

| 2004/0152970 A1 | 8/2004 | Hunter et al. |
| 2013/0060146 A1* | 3/2013 | Yang ...................... A61B 6/032 600/476 |
| 2017/0035517 A1 | 2/2017 | Geri et al. |

FOREIGN PATENT DOCUMENTS

| EP | 1563799 A1 | 8/2005 |
| WO | WO2003077101 A1 | 9/2003 |
| WO | WO2017003916 A1 | 1/2017 |

OTHER PUBLICATIONS

International Search Report and Written Opinion issued in Application No. PCT/EP2017/064625 dated May 15, 2018.
Goerres et al. "Spinal Pedicle Screw Planning Using Deformable Atlas Registration" Institute of Physics and Engineering in Medicine Physics in Medicine and Biology. vol. 62, No. 7. Mar. 14, 2017.
De Silva et al. "Utility of the LevelCheck Algorithm for Decision Support in Vertebral Localization" Spine. vol. 41, No. 20. Mar. 8, 2016.

* cited by examiner

*Primary Examiner* — Christopher J Beccia
(74) *Attorney, Agent, or Firm* — Middleton Reutlinger (57) ABSTRACT

The present invention relates to a computer-implemented medical data processing method, a corresponding computer program and a corresponding system for planning an implant placement into an anatomical structure of a patient, which allows a user to modify the implant placement within a frame defined by predefined requirements that have to be fulfilled for achieving a desired medical outcome.

14 Claims, 5 Drawing Sheets

IMPLANT PLACEMENT PLANNING

TECHNICAL FIELD

The present invention relates to a computer-implemented medical data processing method for planning an implant placement into an anatomical structure of a patient, which allows a user to modify the implant placement within a frame defined by predefined requirements that have to be fulfilled for achieving a desired medical outcome. The present invention further relates to a corresponding computer program and a corresponding system running that program or performing that method.

SUMMARY

In recent years image guided surgery (IGS) has become a technique that helps surgeons in a wide variety of medical procedures, including those which involve planning a placement of an implant or even involve the actual placement of an implant into the body of a patient who is to be treated. Such implants may be permanently placed implants that remain within the patient's body, such as bone-screws connecting or supporting bone tissue, but may also contain prosthetic implants including knee-joint implants and hip-joint implants. The term implant may however also refer to temporarily placed implants such as catheters which are withdrawn from the patient's body again after a medical procedure has finished.

Even though image guided surgery facilitates such procedures, it takes a lot of the surgeon's experience to find the best approach for placing an implant. For example, the surgeon has to make sure that delicate anatomical structures are neither harmed when placing the implant nor by the actual implant itself. In the case of bone-screws or prosthetic implants, further requirements have to be considered in order for the implant to serve its intended purpose. For example, bone-screws and prosthetic implants have to be fitted to a bone structure in such manner that the implant receives sufficient support and will not loosen or even brake away from the bone structure. The necessary decision finding process may be entirely left to the surgeon who rather "free-handedly" determines the implant position. As this requires a lot of experience, navigation systems have been developed which provide a surgeon with some sort of advice for a proper implant placement by calculating one or more proposals for an implant placement that fulfill the necessary requirements. Such approaches however significantly limit the surgeon's freedom in the decision-finding process. The surgeon may either accept the proposed implant placement or, if not entirely content with that proposal, is again left with the burden of manually determining an alternative implant placement all on his own.

A problem to be solved by the invention therefore is to provide the surgeon with a supportive advice when planning the placement of an implant, which however leaves enough space for the surgeon's preferences during said planning process.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention wherever technical expedient and feasible. Specifically, a feature of one embodiment which has the same or a similar function to another feature of another embodiment can be exchanged with said other feature. A feature of one embodiment which adds an additional function to another embodiment can in particular be added to said other embodiment.

According to the present invention a computer-implemented medical data processing method is provided, which is utilized for planning an implant placement into anatomical structure of a patient, and which comprises executing, on a processor of a computer, the following steps:

- a three dimensional image-dataset of the patient is acquired, showing at least the anatomical structure into which the implant is planned to be placed;
- at least one requirement is acquired that has to be fulfilled by the implant when being placed in the anatomical structure so as to achieve a certain medical outcome;
- a frame for possible implant placements is determined, particularly calculated, based on the three-dimensional image-dataset and the at least one requirement, within which a spatial position of the implant with respect to the anatomical structure fulfills the at least one requirement;
- a user input is acquired that involves a manual determination of a final implant placement within the frame for possible implant placements, wherein a current spatial position of the implant is adjusted in correspondence with a determined spatial position of a tracked medical device operated by the user.

In other words, the first two steps of the inventive method are to acquire, on the one hand, a three dimensional patient image which may be obtained from a MR- or a CT-imaging procedure, and to acquire, on the other hand, data as to one or more requirements that have to be fulfilled by a later implant placement. Based on this data acquired and with the help of a processor, a so-called frame for possible implant placements is then determined. This means that a later implant placement fulfills all or, depending on the surgeon's decision, at least most of the set requirements to a certain degree, as long as it is situated within the determined frame.

In this context it is important to note that the frame is already implicitly defined and therefore determined by the entirety of the requirements that have to be fulfilled for the specific patient's anatomy shown in the image data set. It is however also conceivable that such frame is calculated in a specific step as some sort of conjunction of the underlying requirements which may then be replaced by the calculated frame for further processing in the following method steps. Further, the implicitly defined or optionally calculated frame may be understood as an actual geometric frame at the location where the implant has to be placed, wherein the frame defines a border which must, not or at least should not be crossed by the implant.

With such a frame put in place, the surgeon is then free in deciding a final implant placement in accordance with his preferences, but with the limitation given by the frame. In order to ease the "fine-adjustment" of the implant placement, a tracked medical device may be operated, i.e. moved within the three-dimensional space by the user, wherein the current (virtual) spatial position of the implant corresponds to the determined (actual) spatial position of the tracked device moved by the user. More specifically, the patient image may be displayed to the surgeon on a display device of a medical navigation system along with the determined frame and a virtual representation of the medical implant, wherein the surgeon can adjust the spatial position of the implant with respect to the anatomical structure and within the determined frame in real time by moving the tracked device. When moving the device, the surgeon immediately sees the implant correspondingly moving with respect to the anatomical structure, which allows for an easy and fast evaluation of the current implant position.

With the present invention the surgeon is neither left on his own when taking a decision as to an implant placement, but can rather rely on the frame making sure that the set requirements are met. On the other hand, the surgeon is not restricted to a limited number of calculated suggestions for an implant placement, but is still able to adjust an implant placement "on the fly" in accordance with his preferences and experience.

According to a preferred embodiment of the inventive method, the at least one requirement that has to be fulfilled by a later implant placement is selected from the group consisting of:

implant geometry comprising parameters such as the implant's type, size, length, width, diameter shape;

implant position comprising parameters such as the implants spatial location and orientation with respect to the anatomical structure, to a further anatomical structure and/or to at least one further implant to be placed;

safety factors comprising parameter such as prohibited areas and/or areas considered to be critical for an implant placement;

procedure related requirements such as possible geometric arrangements of tools needed for placing the implant or patient posture;

manually defined requirements inputted by the user;

requirements based on predefined literature values, such as predefined implant positions or angles with respect to anatomical landmarks and/or anatomical directions;

and wherein, for a plurality of requirements being acquired, said possible implant placements within the frame fulfill all or at least most of the requirements, particularly wherein the requirements are fulfilled in accordance with a weighting-factor assigned to the requirements acquired.

As in most cases a plurality of requirements has to be fulfilled by an implant placed in an anatomical structure, one or more requirements may exclude each other in some cases, which would ultimate lead to calculated frame that does not allow a single implant placement. In such cases, some requirements may automatically or manually "softened up" to end up with at least one allowable implant placement. Further, it is also conceivable that the requirements are weighted in accordance with the level of importance that the corresponding requirement is fulfilled. As a specific example, the diameter or the length of a bone-screw may be reduced under a predefined limit to make sure that the distal end screw-body does not penetrate the surface of a bone when being placed in said bone.

According to another preferred embodiment the user input may further optionally involve a manual adjustment of the at least one requirement and/or assigned weighting factor. This will again enable the surgeon to soften up the limits for an implant placement, but also enables him to tighten the calculated frame. The surgeon may also alter the ranking of the requirements to be fulfilled.

While the term "implant placement" may well only define the spatial position (spatial location and/or spatial orientation) of an implant, other implant-related parameters of a later implant may be considered. For example, the type, size, length, width, diameter or geometry of an implant may be defined as a further parameter and may be adjusted by a user input to reach a final implant placement. For example, the surgeon may alter the length of an implant on his own initiative even though the former screw length fulfills the set requirements just as well.

According to a further preferred embodiment of the present invention the implant is adapted to be implanted along a linear trajectory, wherein the spatial position of the implant or of the linear trajectory is adjusted by moving the tracked device, and particularly wherein the implant or the linear trajectory remains parallel to a longitudinal axis defined by the tracked device or a predefined point on the implant or the linear trajectory remains at a predefined position with respect to the tracked device, wherein the linear trajectory pivots around a predefined pivot point.

According to this preferred embodiment, the longitudinal axis of the implant itself or of the linear trajectory moves, as it is displayed on a display device of a medical navigation system, in a synchronous manner to the tracked device moved by the surgeon in real space. Consequently, the surgeon can already tell the spatial position (spatial location and/or spatial orientation) of a later implant in real space from the spatial position of the tracked device.

Alternatively, a fixed point on the implant or on the linear trajectory may be defined that remains at a predefined position with respect to a predefined point on the tracked device, wherein the implant or the linear trajectory pivots in correspondence with the position of the tracked device. In order to do so, a pivot point may be defined around which the implant rotates in correspondence with the movement of the tracked device. Further, this pivot point may lie on the implant's longitudinal axis or on the linear trajectory or any other feasible position. The pivot point may stay stationary or may take a variable position during the adjustment procedure. In this manner the surgeon gets the impression that the virtual implant "magnetically" adheres to a predefined point of a tracked device (for example the tip of the device), such that the spatial orientation of the implant or of the linear trajectory can be changed by moving the tracked device in a "parallel" manner with its longitudinal axis remaining unchanged.

As already set out above, the determined frame may constitute a geometric border not to be crossed by an implant. Thus, the calculated frame may even restrain the user input. In other words, the at least one requirement restrains the user input such that the final implant placement fulfills the at least one requirement. Consequently, the virtual implant representation may be moved within the frame up until the implant representation contacts the frame that then prevents a further motion in that direction.

According to an alternative embodiment, such further motion may be permitted, with the implant representation penetrating the frame. Since this represents an inadmissible final placement, a warning message is output to inform the surgeon of an improper implant placement. For example, the implant representation may be shown in a different color, for example red, wherein the unfulfilled requirements may also be displayed.

In a further additional or alternative embodiment of the present invention, at least one parameter of the final implant placement is altered automatically or manually, such that the requirements are fulfilled by the final implant placement. For example, the length of a bone screw may automatically or manually be shortened if the bone-screw would otherwise penetrate the frame with its distal end.

So far, the present invention has been described in the context of planning placement for one single implant. The present invention may however also be utilized for planning a plurality of placements. In this context, an implant may be selected from the plurality of implants for the above-described placement planning by approaching the spatial location and/or the spatial orientation of the implant or its placement trajectory with the tracked device or by aligning the tracked device, with the spatial location and/or the spatial orientation of the implant or the placement trajectory.

In other words, the surgeon may place the virtual representation of the tracked device next to the implant he wants to adjust, or even next to its placement trajectory. The implant or its trajectory will then "snap onto" the virtual device, thus allowing for further adjustment of the implant position. After having determined and fixed the final implant placement, for example by a predefined gesture performed with the tracked device, or by simply pressing a button, the surgeon may proceed with another implant by moving the virtual device next to the further implant or its placement trajectory.

Another preferred embodiment of the present invention involves the use of an anatomical atlas, wherein the at least one requirement is acquired from said atlas registered to the three-dimensional image-data set of the patient. For example, the anatomical atlas may already contain data as to the framework for a plurality of medical implants, such that a registration of the anatomical atlas with the three-dimensional patient image immediately shows required frame(s) or parts of the frame(s) for the specific patient to be treated.

Even though the method according to the present invention may be utilized for planning placement of any implant, planning the placement of bone screws, particularly of pedicle screws constitutes a specifically preferred application for the present invention. Since said screws are set with the help of specifically designed tools, such placement tools may act as the above described tracked medical device. Not being limited to a placement tool for bone screws, the tracked medical device may also be the distal section of an automatic or semi-automatic robotic support arm used during a later surgical procedure.

A further aspect of the present invention relates to a program, which, when running on a computer, causes the computer to perform the method steps of the method according to one of the embodiments described above, and/or a program storage medium on which the program is stored, in particular in a non-transitory form. As it has already indicated in the above description, such computer may form part of a medical navigation system which is used within the framework of image guided surgery. Thus, the present invention further relates to a system for planning an implant placement into an anatomical structure of a patient, which comprises a computer on which the aforementioned program is stored and/or run.

Definitions

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

Steps relating to the acquisition of data for example encompass (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

The invention also relates to a program which, when running on a computer, causes the computer to perform one or more or all of the method steps described herein and/or to a program storage medium on which the program is stored (in particular in a non-transitory form) and/or to a computer comprising said program storage medium and/or to a (physical, for example electrical, for example technically generated) signal wave, for example a digital signal wave, carrying information which represents the program, for example the aforementioned program, which for example comprises code means which are adapted to perform any or all of the method steps described herein.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a navigation system. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

A pointer is a rod which comprises one or more—advantageously, two—markers fastened to it and which can be used to measure off individual co-ordinates, for example spatial co-ordinates (i.e. three-dimensional co-ordinates), on a part of the body, wherein a user guides the pointer (for example, a part of the pointer which has a defined and advantageously fixed position with respect to the at least one marker attached to the pointer) to the position corresponding to the co-ordinates, such that the position of the pointer can be determined by using a surgical navigation system to detect the marker on the pointer. The relative location between the markers of the pointer and the part of the pointer used to measure off co-ordinates (for example, the tip of the pointer) is for example known. The surgical navigation system then enables the location (of the three-dimensional co-ordinates) to be assigned to a predetermined body structure, wherein the assignment can be made automatically or by user intervention.

A navigation system, such as a surgical navigation system, is understood to mean a system which can comprise: at least one marker device; a transmitter which emits electromagnetic waves and/or radiation and/or ultrasound waves; a receiver which receives electromagnetic waves and/or radiation and/or ultrasound waves; and an electronic data processing device which is connected to the receiver and/or the transmitter, wherein the data processing device (for example, a computer) for example comprises a processor (CPU) and a working memory and advantageously an indicating device for issuing an indication signal (for example, a visual indicating device such as a monitor and/or an audio indicating device such as a loudspeaker and/or a tactile indicating device such as a vibrator) and a permanent data memory, wherein the data processing device processes navigation data forwarded to it by the receiver and can advantageously output guidance information to a user via the indicating device. The navigation data can be stored in the permanent data memory and for example compared with data stored in said memory beforehand.

A landmark is a defined element of an anatomical body part which is always identical or recurs with a high degree of similarity in the same anatomical body part of multiple patients. Typical landmarks are for example the epicondyles of a femoral bone or the tips of the transverse processes and/or dorsal process of a vertebra. The points (main points or auxiliary points) can represent such landmarks. A landmark which lies on (for example on the surface of) a characteristic anatomical structure of the body part can also represent said structure. The landmark can represent the anatomical structure as a whole or only a point or part of it. A landmark can also for example lie on the anatomical structure, which is for example a prominent structure. An example of such an anatomical structure is the posterior aspect of the iliac crest. Another example of a landmark is one defined by the rim of the acetabulum, for instance by the centre of said rim. In another example, a landmark represents the bottom or deepest point of an acetabulum, which is derived from a multitude of detection points. Thus, one landmark can for example represent a multitude of detection points. As mentioned above, a landmark can represent an anatomical characteristic which is defined on the basis of a characteristic structure of the body part. Additionally, a landmark can also represent an anatomical characteristic defined by a relative movement of two body parts, such as the rotational center of the femur when moved relative to the acetabulum.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises positional information which can be matched (for example by applying an elastic or rigid image fusion algorithm) for example to positional information contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

In particular, the invention does not involve or in particular comprise or encompass an invasive step which would represent a substantial physical interference with the body requiring professional medical expertise to be carried out and entailing a substantial health risk even when carried out with the required professional care and expertise. For example, the invention does not comprise a step of positioning a medical implant in order to fasten it to an anatomical structure or a step of fastening the medical implant to the anatomical structure or a step of preparing the anatomical structure for having the medical implant fastened to it. More particularly, the invention does not involve or in particular comprise or encompass any surgical or therapeutic activity. The invention is instead directed as applicable to positioning a tool relative to the medical implant, which may be outside the patient's body. For this reason alone, no surgical or therapeutic activity and in particular no surgical or therapeutic step is necessitated or implied by carrying out the invention.

The present invention may be implemented with any IGS system. In particular the present invention may form an integrated part of "iPlan®", a Brainlab® product.

BRIEF DESCRIPTION OF DRAWINGS

In the following, the invention is described with reference to the enclosed figures which represent preferred embodiments of the invention. The scope of the invention is however not limited to the specific features disclosed in the figures, which show.

DETAILED DESCRIPTION

Figure 1:
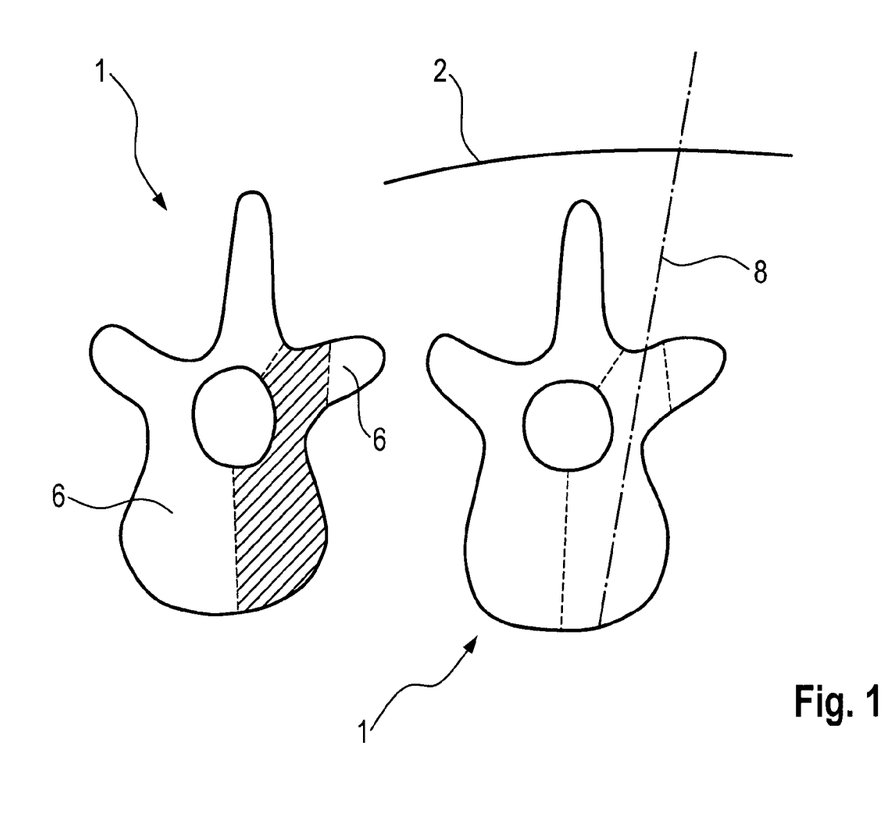
FIG. 1 a vertebra in which a pedicle screw has to be placed at a desired location.

FIG. 1 shows a vertebra 1 of a patient 2, into which a pedicle screw 3 is planned to be implanted. The pedicle screw 3 that has to be implanted into the right pedicle. A designated vertebra sector (hatched area) is defined within which the pedicle screw 3 has to be placed. This means that other areas 6 have to be avoided (as a requirement) and are therefore defined as prohibited areas 6.

In the context of the present invention, an initial proposal for a possible screw placement may be calculated and shown on a display, which is represented by the placement trajectory 8 shown in FIG. 1. While the vertebra image is taken from a three-dimensional image data set of the patient 2 that has been acquired beforehand, the prohibited areas 6 and the initial suggestion for a placement trajectory 8 shown in FIG. 1 has been taken from an anatomical atlas that has already been matched to the vertebra 1.

Figure 2:
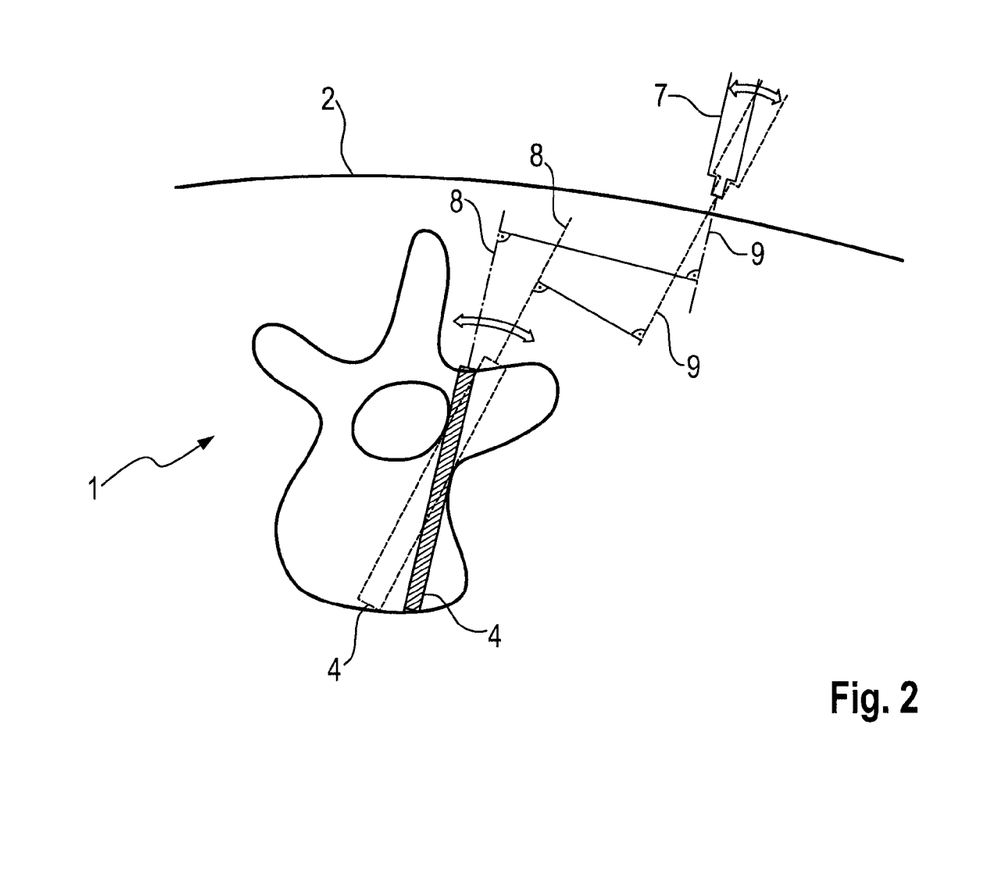
FIG. 2 an adjustment of the implant's spatial position within a determined frame.

As shown in FIG. 2, the surgeon may manipulate the possible implant placement 4 as long as it stays within the determined frame, i.e. does not enter the prohibited areas 6. In order to do so, the surgeon holds a hand-held screw-placement tool 7 next to the vertebra 1, such that the placement trajectory 8 "snaps on" to the longitudinal axis 9 of the tool 7. By pivoting the tool 7, the surgeon also pivots the virtual representation of the screw 3. Since a further requirement for the screw is to not penetrate the vertebra surface, the possible implant placement automatically pivots within the constricted pedicle, but still stays within the allowed sector/frame shown in FIG. 1.

Figure 3:
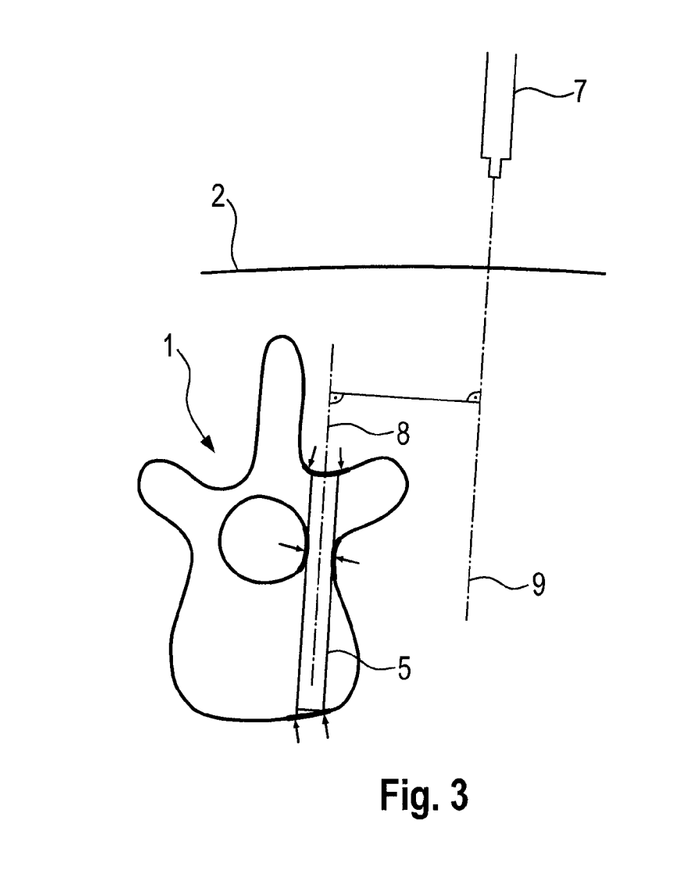
FIG. 3 a final implant placement determined by the surgeon.

After a desired implant placement has been reached, the surgeon may designate it as a final implant placement 5 (shown in FIG. 3) by performing a predefined gesture such as turning the tool 7 around its longitudinal axis 9, or by simply pressing button.

Figure 4:
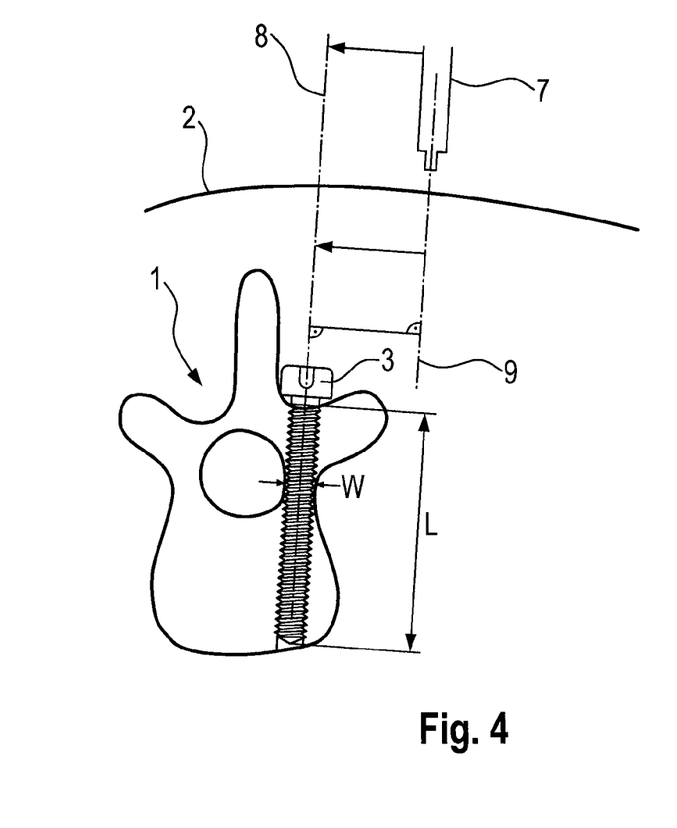
FIG. 4 a pedicle screw in its final position.

In a later procedure indicated in FIG. 4, the longitudinal axis 9 of the placement tool 7 merely needs to be brought from a parallel arrangement with respect to a placement trajectory 8 to a position where it aligns with the placement trajectory 8, such that the screw 3 can be easily screwed into its designated position within the vertebra 1 without even tilting the tool 7.

Figure 5:
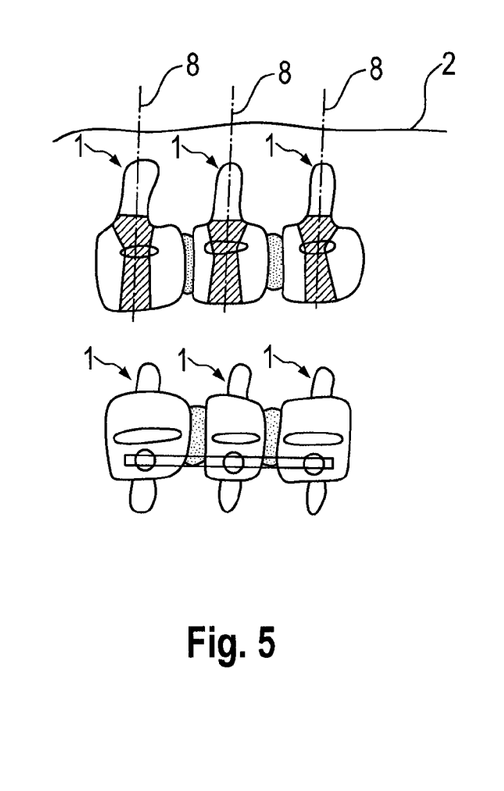
FIG. 5 adjacent vertebrae of a spinal column being stabilized by pedicle screws and connecting rods.

For a plurality of screws 3 to be placed into an arrangement of vertebrae 1 so as to stabilize a certain part of a spinal column, the procedure as described above is performed several times for each screw 3. It is however important to note that, since the pedicle screws 3 are connected by a stabilizing rod, each determination of a final screw placement effects the other determinations of final screw placements. Thus, placement planning has to consider the geometric restrictions caused by the connecting rod as a further requirement to be fulfilled by each screw placement.

Figure 6:
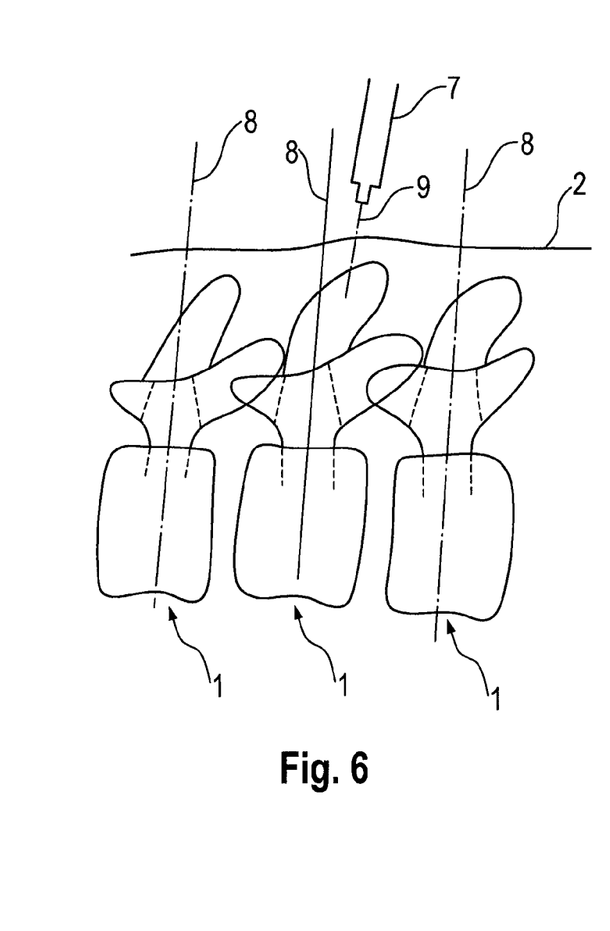
FIG. 6 the selection of a specific implant from a plurality of implants.

FIG. 6 shows the course of planning a plurality of implant placements. In order to plan placement into a specific vertebra 1, the surgeon moves the tool 7 next to the desired vertebra 1 and aligns the tool's longitudinal axis 9 with the already suggested and displayed placement trajectory 8. After having determined a satisfying final screw placement for that vertebra 1, the surgeon may then continue with approaching the next vertebra 1 with the tool 7. FIG. 6 also shows that during the entire procedure the tool 7 stays above the skin of the patient 2 and moves along the spinal column to consecutively run through the arrangement of vertebrae 1.

Figure 7:
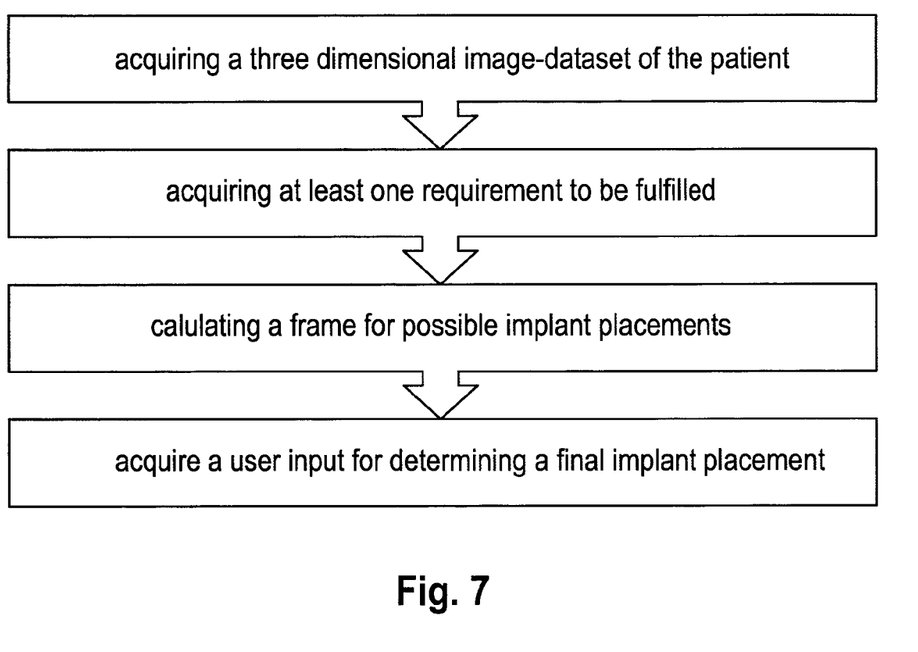
FIG. 7 the basic method steps of the inventive method.

FIG. 7 shows the basic steps of specific embodiment the inventive planning method, wherein the first two steps, namely acquiring the patient image data and acquiring data as to requirements to be fulfilled by a later placement of an implant, forms the basis for the following third step of calculating a frame for possible implant placements. Within that calculated frame, the user can then manipulate and eventually determine a final implant placement which is acquired via a user input.

The invention claimed is:

1. A computer-implemented method for planning an implant placement into an anatomical structure of a patient, wherein the method comprises executing, on at least one processor, the following steps:

acquiring a three-dimensional image-dataset of the patient showing at least the anatomical structure into which the implant is planned to be placed;

acquiring at least one requirement that has to be fulfilled by the implant when being placed in the anatomical structure so as to achieve a medical outcome;

acquiring a user input that involves determining a spatial position of a tracked medical device operated by a user, wherein a current spatial position of a virtual implant representation is adjusted in correspondence with the determined spatial position of the tracked medical device calculating a frame and an initial proposal for possible implant placements based on the three-dimensional image-dataset and the at least one requirement, wherein, within the frame, a spatial position of the implant with respect to the anatomical structure fulfills the at least one requirement of not entering a prohibited area of the anatomical structure, and wherein the initial proposal for a possible implant placement is shown on a display determining a current spatial position of the virtual implant representation as a final implant placement via a user input, wherein the final implant placement is within the frame for possible implant placements.

2. The method according to claim 1, wherein the at least one requirement is selected from at least one of:

implant geometry comprising parameters such as the implant's type, size, length, width, diameter, shape or geometry;

implant position comprising parameters such as the implant's spatial location and orientation with respect to the anatomical structure, to a further anatomical structure and/or to at least one further implant to be placed;

safety factors comprising parameter such as prohibited areas and/or areas considered to be critical for the implant placement;

procedure related requirements such as possible geometric arrangements of tools needed for placing the implant or patient posture;

manually defined requirements inputted by the user;

requirements based on predefined values, such as predefined implant positions or angles with respect to anatomical landmarks and/or anatomical directions; and wherein, for a plurality of requirements being acquired, said possible implant placements within the frame fulfill all or at least most of the requirements, particularly wherein the requirements are fulfilled in accordance with a weighting-factor assigned to the requirements acquired.

3. The method according to claim 1, wherein the user input further optionally involves a manual adjustment of the at least one requirement and/or assigned weighting-factor.

4. The method according to claim 1, wherein, in addition to the spatial position of the implant, implant specifications such as possible implant type size, length, width shape, diameter or geometry are defined as an implant-related parameter by the frame.

5. The method according to claim 1, wherein the implant is adapted to be implanted along a linear trajectory, wherein the spatial position of the implant or of the linear trajectory is adjusted by moving the tracked medical device, and particularly wherein the implant or the linear trajectory remains parallel to a longitudinal axis defined by the tracked medical device or a predefined point on the implant or the linear trajectory remains at a predefined position with respect to the tracked medical device, wherein the implant or the linear trajectory pivots in correspondence with the predefined position of the tracked medical device.

6. The method according to claim 1, wherein the user input is restrained by the at least one requirement such that the final implant placement fulfills the at least one requirement.

7. The method according to claim 1, wherein, when a user input results in the final implant placement that does not fulfill a requirement, a warning message is output indicating the unfulfilled requirement and/or the improper final implant placement.

8. The method according to claim 1, wherein, when a user input results in the final implant placement that does not fulfill a requirement, at least one parameter of the final implant placement is altered such that the requirements are fulfilled by the final implant placement.

9. The method according to claim 5, wherein implant placements into anatomical structures of the patient are planned for a plurality of implants, and wherein an implant is selected from the plurality of implants for placement planning by approaching the spatial position and/or spatial orientation of the implant or its placement trajectory with the tracked medical device and/or by aligning the tracked medical device with the spatial position and/or the spatial orientation of the implant or the placement trajectory.

10. The method according to claim 1 wherein the at least one requirement is acquired from an anatomical atlas registered to the three-dimensional image-dataset of the patient.

11. The method according to claim 1, wherein the implant that is a bone screw and/or wherein the tracked medical device is a placement tool used for placing a screw.

12. A system operating on at least one processor, comprising:

a medical navigation system operating on the at least one processor having associated memory with program instructions, the instructions, when executed, operable to:

acquire a three-dimensional image-dataset of a patient showing at least an anatomical structure into which the implant is planned to be placed;

acquire at least one requirement that has to be fulfilled by the implant when being placed in the anatomical structure so as to achieve a medical outcome;

acquire a user input that involves determining a spatial position of a tracked medical device operated by a user, wherein a current spatial position of a virtual implant representation is adjusted in correspondence with the determined spatial position of the tracked medical device;

calculate a frame and an initial proposal for possible implant placements based on the three-dimensional image-dataset and the at least one requirement, wherein, within the frame, a spatial position of the implant with respect to the anatomical structure fulfills the at least one requirement of not entering a prohibited area of the anatomical structure, and wherein the initial proposal for a possible implant placement is shown on a display;

determine a current spatial position of the virtual implant representation as a final implant placement via a user input, wherein the final implant placement is within the frame for possible implant placements;

wherein the medical navigation system is operating within the framework of an IGS-procedure.

13. A non-transitory computer-readable storage medium storing a computer program which, when executed on at least one processor of at least one computer, causes the at least one computer to perform the steps comprising:

acquiring a three-dimensional image-dataset of a patient showing at least an anatomical structure into which the implant is planned to be placed;

acquiring at least one requirement that has to be fulfilled by the implant when being placed in the anatomical structure so as to achieve a medical outcome;

acquiring a user input that involves determining a spatial position of a tracked medical device operated by a user, wherein a current spatial position of a virtual implant representation is adjusted in correspondence with the determined spatial position of the tracked medical device calculating a frame and an initial proposal for possible implant placements based on the three-dimensional image-dataset and the at least one requirement, wherein, within the frame, a spatial position of the implant with respect to the anatomical structure fulfills the at least one requirement of not entering a prohibited area of the anatomical structure, and wherein the initial proposal for a possible implant placement is shown on a display;

determining a current spatial position of the virtual implant representation as a final implant placement via a user input, wherein the final implant placement is within the frame for possible implant placements.

14. A system for planning an implant placement into an anatomical structure of a patient, comprising:

at least one processor having associated memory with program instructions, the instructions, when executed, operable to:

acquire a three-dimensional image-dataset of the patient showing at least the anatomical structure into which the implant is planned to be placed;

acquire at least one requirement that has to be fulfilled by the implant when being placed in the anatomical structure so as to achieve a medical outcome;

acquire a user input that involves determining a spatial position of a tracked medical device operated by a user, wherein a current spatial position of a virtual implant representation is adjusted in correspondence with the determined spatial position of tracked medical device calculate a frame and an initial proposal for possible implant placements based on the three-dimensional image-dataset and the at least one requirement, wherein, within the frame, a spatial position of the implant with respect to the anatomical structure fulfills the at least one requirement of not entering a prohibited area of the anatomical structure, and wherein the initial proposal for a possible implant placement is shown on a display;

determine a current spatial position of the virtual implant representation as a final implant placement via a user input, wherein the final implant placement is within the frame for possible implant placements.

* * * * *